United States Patent [19]

Ohnishi et al.

[11] 4,215,230
[45] Jul. 29, 1980

[54] PRODUCTION OF IONONES AND IRONES BY THERMAL REARRANGEMENT OF PROPARGYLIC ALCOHOLS

[75] Inventors: Takashi Ohnishi; Yoshiji Fujita; Michihiro Ishiguro; Takashi Nishida, all of Kurashiki, Japan

[73] Assignee: Kuraray Co., Ltd., Kurashiki, Japan

[21] Appl. No.: 908,818

[22] Filed: May 23, 1978

[30] Foreign Application Priority Data

May 23, 1977 [JP] Japan ................... 52-60112
May 23, 1977 [JP] Japan ................... 52-60113

[51] Int. Cl.² .............. C07C 45/00; C07C 33/05; C07C 33/04; C07C 33/02
[52] U.S. Cl. ................... 568/341; 568/824; 568/826
[58] Field of Search ............. 260/586 R; 568/824, 568/826

[56] References Cited

U.S. PATENT DOCUMENTS

| 2,382,086 | 8/1945 | Milas | 568/824 |
| 2,472,310 | 6/1949 | Oroshnik | 568/824 |
| 2,540,116 | 2/1951 | Haber et al. | 568/824 |
| 2,567,572 | 9/1951 | Milas | 568/824 |
| 2,676,990 | 4/1954 | Humphfett et al. | 568/824 |
| 3,445,534 | 5/1969 | Bach et al. | 568/824 |
| 3,852,355 | 12/1974 | Rautenstrauch et al. | 260/586 R |
| 3,887,625 | 6/1975 | Schulte-Elte | 260/586 R |
| 3,892,809 | 7/1975 | Schulte-Elte | 260/586 R |

OTHER PUBLICATIONS

Freser et al., "Reagents for Org. Syn.", p. 389, (1967), John Wiley & Sons, Inc.
Berson et al., "J.A.C.S.", 86, 5019, 5017, (1964).
Viola et al., "J.A.C.S.", 87, 1150, (1965).
Viola et al., "J.A.C.S.", 92, 2404, (1970).

Primary Examiner—Norman Morgenstern
Attorney, Agent, or Firm—Burns, Doane, Swecker & Mathis

[57] ABSTRACT

Ionones and irones are produced by thermal rearrangement of novel propargylic alcohols, as follows:

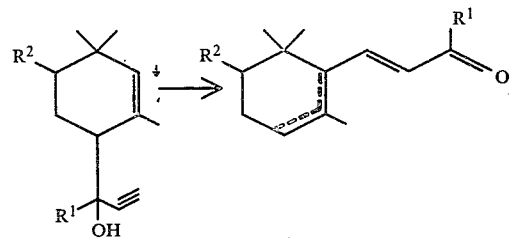

wherein $R^1$ is a lower alkyl group, $R^2$ is hydrogen or methyl and the dotted lines in the product formula reflect the existence of a double bond at either one or the other of the positions indicated.

8 Claims, No Drawings

PRODUCTION OF IONONES AND IRONES BY THERMAL REARRANGEMENT OF PROPARGYLIC ALCOHOLS

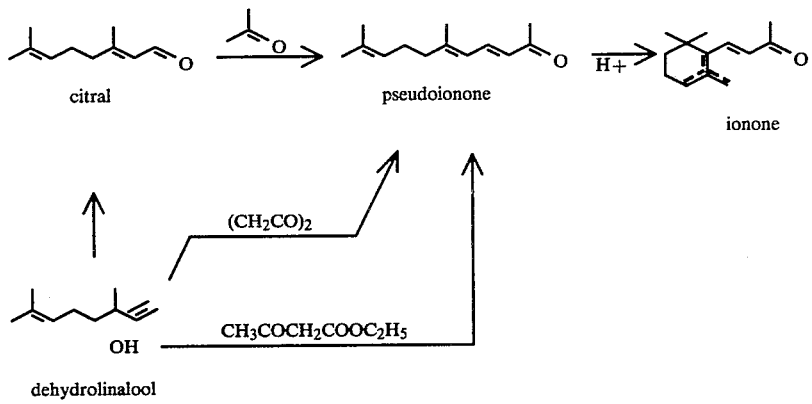

citral pseudoionone ionone dehydrolinalool

BACKGROUND OF THE INVENTION

1. Field of the Invention

The present invention relates to a method for producing ionones or irones, or n-derivatives thereof, through the thermal rearrangement of certain novel propargylic alcohols. This invention also relates to such starting material propargylic alcohols.

2. Description of the Prior Art

The rearrangement of a propargylic alcohol to an unsaturated ketone under the influence of heat is generally known as the "Oxy-Cope rearrangement". However, the particular propargylic alcohols which are used in the present invention have not been subjected to an Oxy-Cope rearrangement, nor it is known that ionones and irones can be produced by this reaction. Briefly, the prior art relevant to an Oxy-Cope rearrangement reaction will now be reviewed. "Oxy-Cope rearrangement" is a term which was coined by J. A. Berson et al who studied this reaction with cyclic compounds [*J. Am. Chem. Soc.*, 86, 5017 and 5019 (1964)]. Later, A. Viola et al studied the reaction of acyclic compounds in gaseous phase [*J. Am. Chem. Soc.*, 87, 1150 (1965)]. Thereafter, a number of workers did theoretical and applied research on this reaction. However, as far as propargylic alcohols and their uses are concerned, only A. Viola et al [*J. Am. Chem. Soc.*, 92, 2404 (1970)] are known to have utilized this reaction. They obtained the unsaturated aldehyde

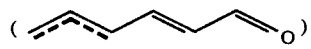

by heating 5-hexen-1-yn-3-ol

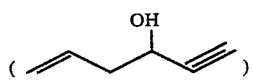

in a gaseous phase at 350° to 390° C.

Ionone has heretofore been commercially produced by cyclizing pseudoionone, which is obtained by the condensation of citral with acetone, or the reaction of dehydrolinalool with ethyl acetoacetate or diketene involving Carroll rearrangement, under the influence of a comparatively large amount of acid such as sulfuric acid or phosphoric acid [cf. U.S. Pat. Nos. 3,480,677 and 3,886,215, for example]. The reaction may be illustrated by the following scheme.

In the above formula of ionone, the dotted lines represent a double bond in one or the other of the indicated positions. Irone is obtained by using 3,6,7-trimethyl-2,6-octadien-1-al in lieu of citral in the above reaction, or 3,6,7-trimethyl-1-octyn-6-en-3-ol in lieu of dehydrolinalool in the above reaction. The production of ionones or irones via the cyclization of pseudoionones or pseudoirones presents the problem of reactor corrosion due to the use of a comparatively large amount of acidic cyclizing agent. It is also not easy to dispose of the acid-containing waste solution.

Alkyl-substituted ionones such as methylionone are produced by condensing an alkyl-substituted acetone, e.g., methyl ethyl ketone with citral and subsequently cyclizing the reaction product. Of course, the products are mixtures of normal- and iso-alkyl-substituted ionones [cf. U.S. Pat. No. 2,877,271, for example]. The reactions may be illustrated as follows:

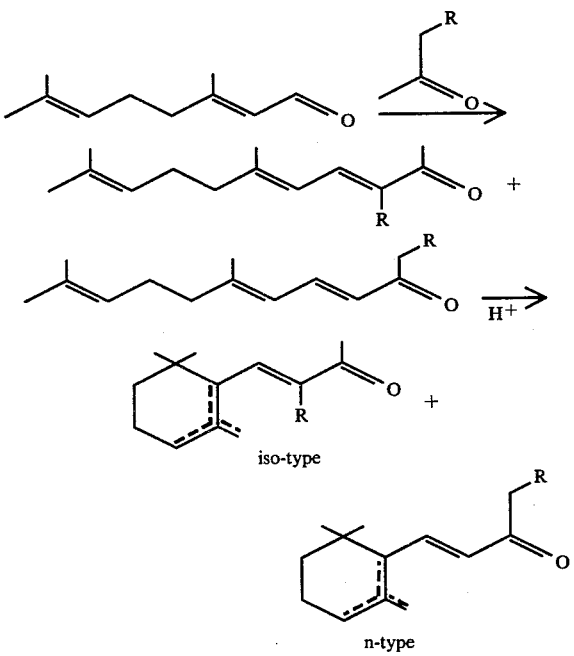

iso-type n-type (wherein R is a lower alkyl group)

Another prior art method for producing ionone commences with 2,6,6-trimethylcyclohexanone and comprises a combination of ethynylation reaction, dehydration reaction and Grignard reaction [U.S. Pat. No. 3,886,215 and *J. American Chemical Society*, 71, 4136 (1949)].

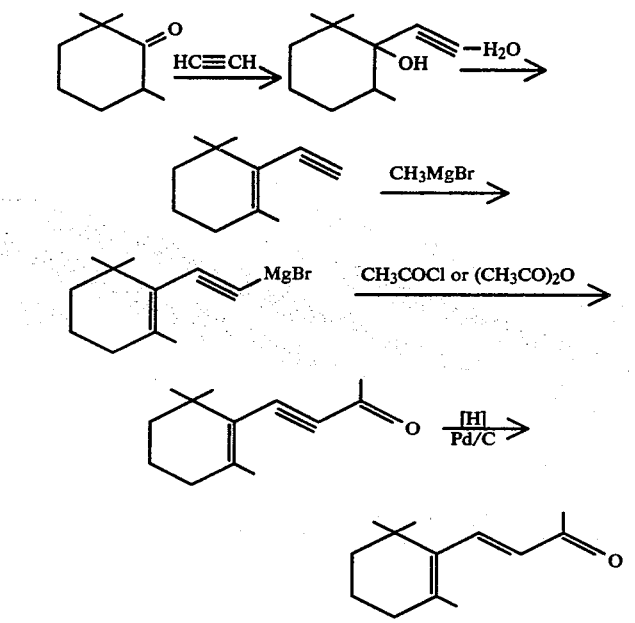

The above method is of little practical value because of the problems that [1] the starting material 2,6,6-trimethylcyclohexanone is not readily available, [2] the dehydration reaction of the ethynylation product of said cyclohexanone is low in selectivity and [3] the process involves a fairly large number of steps.

SUMMARY OF THE INVENTION

Accordingly, a primary object of this invention is to provide a novel method for producing ionones and irones which is essentially different from the prior art processes hereinbefore mentioned. The method of the present invention, moreover, overcomes the difficulties associated with the prior art.

Another object of the invention is to provide novel propargylic alcohols at the starting materials to be used in the above method.

Briefly, in accordance with the present invention, compounds of the following general formula (I):

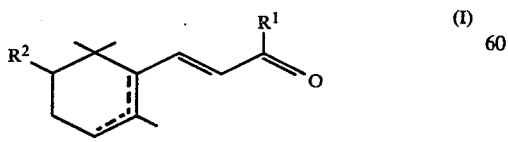

are produced by the thermal rearrangement reaction of propargylic alcohols of the following general formula (II):

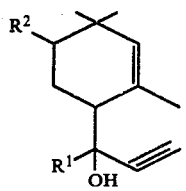

In the above formulas (I) and (II), $R^1$ is a lower alkyl group containing 1 to 5 carbon atoms, such as methyl, ethyl, n-propyl, isopropyl, n-butyl, isobutyl, isoamyl, etc.; $R^2$ is hydrogen or methyl; the dotted lines in formula (I) mean that a double bond exists in either one of the indicated positions. Thus, the compound produced according to the invention is ionone when $R^1$ is methyl and $R^2$ is hydrogen; irone when both $R^1$ and $R^2$ are methyl; or an n-derivative of ionone or irone when $R^2$ is hydrogen or methyl and $R^1$ is a lower alkyl group of 2 or more carbon atoms.

As mentioned hereinbefore, the rearrangement of a propargylic alcohol to the isomeric unsaturated ketone by heating is known per se as Oxy-Cope rearrangement. The present invention is characterized by the application of said Oxy-Cope rearrangement reaction to the propargylic alcohols of formula (II) for the production of ionones and irones, and features the synthesis of ionones or irones by mere heating without employing an acidic cyclizing agent, and is further characterized in that alkyl ionones and alkyl irones of n-type alone are selectively obtained without giving rise to those of iso-type in the reaction product.

DETAILED DESCRIPTION OF THE INVENTION

The following specific compounds are preferred examples of the propargylic alcohols (II) which may be employed in the practice of the present invention. It should be understood that, regarding the compound names given, "trimethylcyclohexenyl" is an abbreviation of 2',4',4'-trimethyl-2'-cyclohexen-1'-yl and "tetramethylcyclohexenyl" is an abbreviation of 2',4',4',5'-tetramethyl-2'-cyclohexen-1'-yl. It should be further understood that the stereoisomers of the propargylic alcohols of formula (II) [due to their respective asymmetric carbon atoms] are not in and of themselves illustrated, but same are nonetheless within the ambit of the present invention. Such isomers, moreover, are in any event successfully utilized in the practice of the invention.

3-(Trimethylcyclohexenyl)-1-butyn-3-ol (1)

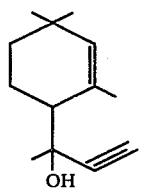

3-(Trimethylcyclohexenyl)-1-pentyn-3-ol (2)

-continued

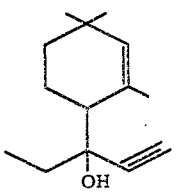

3-(Trimethylcyclohexenyl)-1-hexyn-3-ol (3)

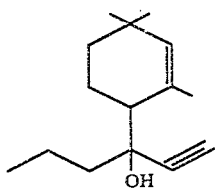

3-(Trimethylcyclohexenyl)-1-heptyn-3-ol (4)

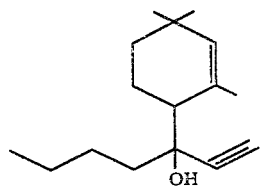

3-(Trimethylcyclohexenyl)-4-methyl-1-pentyn-3-ol (5)

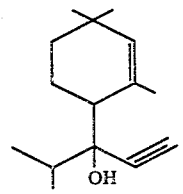

3-(Trimethylcyclohexenyl)-5-methyl-1-hexyn-3-ol (6)

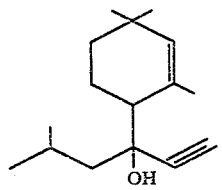

3-(Tetramethylcyclohexenyl)-1-butyn-3-ol (7)

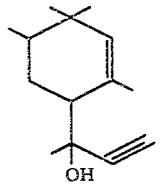

In view of the many uses for their rearrangement products according to the present invention, the propargylic alcohols numbered (1), (2) and (7) above are particularly important.

The rearrangement reaction of a propargylic alcohol of formula (II) can be conducted in liquid phase or gaseous phase. While the reaction may be conducted at an optional temperature in the range of 100° to 400° C., the temperatures preferred from the viewpoints of reaction rate and selectivity are 130° to 300° C. and, for still better results, 150° to 250° C. for a liquid-phase reaction, and 250° to 400° C. for a gaseous phase reaction, although same in fact depends on the residence time.

The reaction may be carried out in an ambient atmosphere. However, it is preferably conducted in an atmosphere of inert gas such as nitrogen or helium. In conducting the reaction in liquid phase, the use of a solvent is not essential, although use may be made of an inert solvent which will remain stable under the conditions of the rearrangement reaction and which will not be involved in the reaction, or one which will contribute to improved selectivity. The reaction pressure is not particularly critical, the reaction normally proceeding satisfactorily at atmospheric pressure. If necessary, the reaction may be conducted at elevated or reduced pressure. Since the subject reaction is a thermal reaction, the reaction time necessary for an attainment of the desired degree of conversion varies with different temperatures.

The rearrangement reaction product is normally a mixture of an α-isomer of the following formula (I-α) and a β-isomer of the formula (I-β) and the proportions of these isomers are dependent upon the conditions of the rearrangement reaction and is also dependent upon the type of solvent used, if any.

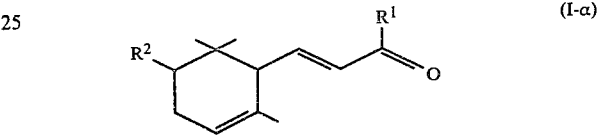 (I-α)

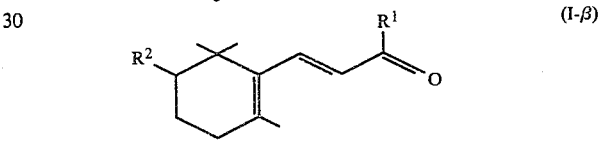 (I-β)

The products according to the present invention, e.g., ionone, n-methyl ionone and irone, are useful for the same purposes as the corresponding products obtained by conventional methods, such as perfumes, intermediates for the production of pharmaceutical products and intermediates for the production of agricultural chemicals.

The propargylic alcohols (II) used as the starting material in the practice of this invention can be prepared by ethynylating an unsaturated ketone represented by the following formula (III):

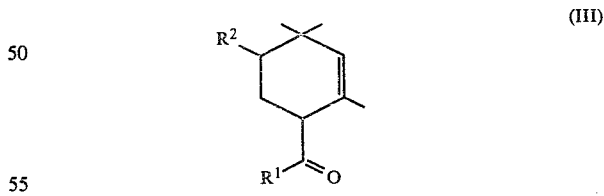 (III)

[wherein $R^1$ and $R^2$ have the same meanings as defined in Formula (I)].

Any ethynylation process capable of converting the unsaturated ketone (III) to the propargylic alcohol (II) may be employed. In view of the operational simplicity and the high selectivity of the reaction, it is particularly desirable to employ a process which comprises reacting an unsaturated ketone of formula (III) with an ethynyl-Grignard reagent, e.g., ethynyl magnesium halide (the halide may be chloride, bromide or iodide) in an appropriate ethereal solvent, such as tetrahydrofuran which is particularly desirable. For example, when the ethynyl magnesium halide is used in an amount of from 1 to 1.5 equivalents of said unsaturated ketone, the propargylic alcohol (II) is obtained in a yield not less than 75%. The ethynyl-Grignard reagent may be prepared in situ or beforehand in the above-mentioned solvent.

The unsaturated ketone (III) may contain an isomer of the following general formula (III') with respect to the position of the double bond.

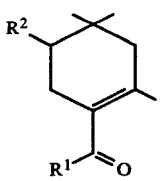

(III')

However, the propargylic alcohol of the following formula (II'), which is produced on ethynylation of the above isomer (III'), is not thermally rearranged into an ionone or irone compound of formula (I).

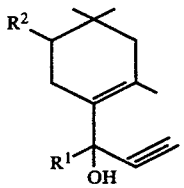

(II')

Therefore, for the purposes of this invention, it is preferable that the isomers of formula (III') be removed or not produced. The separation of these isomers can be effected by distillation.

The process for the production of the unsaturated ketone (III) does not per se constitute an essential part of the invention, nor is the invention limited to any specific process for the production of said ketone. However, for a better understanding of the practicability of the total synthesis of ionones and irones in which the process of the present invention is incorporated, the method of producing an unsaturated ketone of formula (III) will hereinafter be described.

A recommended process for producing an unsaturated ketone of formula (III) comprises reacting a trimethyl- or tetramethylcyclohexene [hereinafter sometimes referred to simply as polymethylcyclohexene] of general formula (IV):

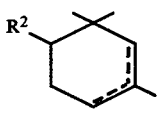

(IV)

[wherein R² and the dotted lines have the same meanings as defined in formula (I)] with an acid halide or acid anhydride of general formula (V):

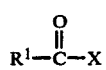

(V)

[wherein R¹ has the same meaning as defined in formula (I); X is halogen or

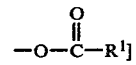

in the presence of a Lewis acid catalyst.

The acylation reaction of cyclo-olefinic compounds in the presence of a Lewis acid catalyst is known [cf. *J. Chem. Soc.*, 2215 (1968), *Tetrahedron Letters*, 3607 (1971), *Tetrahedron*, 24, 1385 (1968), for example]. The acylation reaction of polymethylcyclohexene (IV) with an acid halide or acid anhydride of formula (V) may be carried out in conventional manner and, as said Lewis acid catalyst, zinc chloride, aluminum chloride, tin tetrachloride, boron trifluoride, polyphosphoric acid, or the like, may be successfully employed. The acid halide or acid anhydride of formula (V) should be so selected that it will lead to the desired product of formula (I). Thus, these acid anhydrides and acid halides include acetyl chloride, acetyl bromide, propionyl chloride, propionyl bromide, butyryl chloride, butyryl bromide, isobutyryl chloride, valeryl chloride, acetic anhydride, propionic anhydride, butyric anhydride, isobutyric anhydride, valeric anhydride, etc.

Generally, polymethylcyclohexenes are available as a mixture of isomers with respect to the position of the double bond, as indicated by the dotted lines in formula (IV). Such isomers may be separated from each other, if necessary. However, it is more advantageous to use the isomeric mixture as such for the reaction, because the acylation is not influenced by the position of the double bond. The reaction is generally conducted using 1 to 2 mols of acid halide or acid anhydride (V) per mol of polymethylcyclohexene (IV) in the presence of up to 1.5 mols of a Lewis acid catalyst per mol of polymethylcyclohexene (IV). A suitable reaction temperature should be properly selected according to the particular catalyst employed. Taking zinc chloride as an example of catalyst for the reaction of polymethylcyclohexene with an acid anhydride, the temperature may range from −30° C. to +100° C., preferably between 0° C. to 30° C. In the case of polyphosphoric acid instead of zinc chloride, the range of 50° to 150° C. is suitable. The acylation reaction product is normally a mixture of unsaturated ketones of formula (III) and formula (III'). The proportions of the formed unsaturated ketones (III) and (III') are not dictated by the relative amounts of said polymethylcyclohexene isomers (IV) but are largely influenced by the kind of Lewis acid catalyst employed. For example, when zinc chloride is used as the catalyst, the unsaturated ketone of formula (III) is normally obtained in a proportion of at least 90%, whereas the unsaturated ketone of formula (III') is the dominant product when polyphosphoric acid is employed. As mentioned hereinbefore, the propargylic alcohol (II') to be derived from the unsaturated ketone (III') by ethynylation reaction does not give ionone or irone or an n-derivative thereof (I) by the thermal rearrangement of the present invention. In view of this fact, the acylation reaction is preferably conducted under conditions such that the unsaturated ketone of formula (III) will be produced in as high a yield as possible.

Another process for producing an unsaturated ketone of formula (III), as shown below, comprises condensing a prenyl halide or 2,3-dimethyl-1-halo-2-butene of formula (VII) with mesityl oxide and/or isomesityl oxide in the presence of an alkaline condensing agent such as sodium hydroxide or potassium hydroxide in the manner described in U.S. Pat. Nos. 3,668,255 and 3,983,175 and British Pat. Nos. 851,658 and 1,059,839 and, then, cyclizing the resultant unsaturated ketone of formula (VI) with the aid of phosphoric acid:

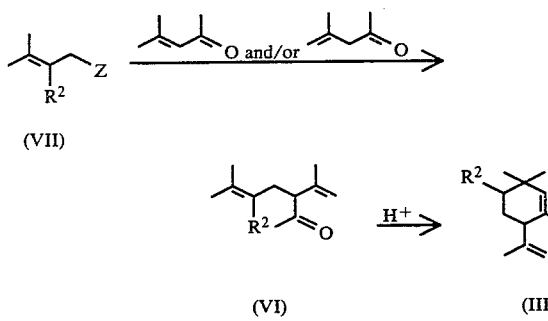

[wherein R² has the same meaning as defined in formula (I); Z is a halogen atom].

In order to further illustrate the present invention and the advantages thereof, the following specific examples are given, it being understood that same are intended only as illustrate, and in nowise limitative.

EXAMPLE 1

(1) Production of unsaturated ketone (III)

A three-necked flask of 400 ml capacity was charged with 24.8 g (0.2 mol) of cyclogeraniolene, 24.4 g (0.24 mol) of acetic anhydride and 32.6 g (0.24 mol) of anhydrous zinc chloride and the contents were stirred at room temperature for 15 hours. After the reaction had been completed, the reaction mixture was poured in ice-water and extracted with ether. The extract was neutralized with a 10% aqueous solution of sodium carbonate, rinsed with water a few times and dried over anhydrous magnesium sulfate. The ether was removed from the extract by a rotary evaporator and the residue was distilled under reduced pressure. The unsaturated ketone formed was recovered as a fraction boiling at 60°–62° C./0.13–0.15 mmHg (30.2 g). This fraction was a mixture of (III) and (III') [(III)/(III')=94/6], where R¹ is methyl and R² is hydrogen. The predominant component of this mixture, [(2',4',4'-trimethyl-2'-cyclohexen-1'-yl)-methylketone], was identified as follows:

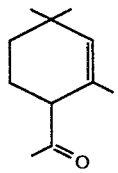

Nuclear magnetic resonance spectrum ($\delta_{ppm}^{in\ CCl_4}$)
5.29(1H,bs), 2.86(1H,t), 2.01(3H,s), 1.51(3H,s), 0.93(3H,s), 0.88(3H,s)

(2) Production of propargylic alcohol (II)

In a three-necked flask of 500 ml capacity, 16.6 g (0.1 mol) of the above mixture of unsaturated ketones was added dropwise at room temperature to 200 ml of a previously prepared tetrahydrofuran solution containing 0.12 mol of ethynylmagnesium bromide. The mixture was stirred at 50°–60° C. for one hour, after which it was mixed with ice-water. After dilute sulfuric acid was added to the mixture to remove the white turbidity, the mixture was extracted with ether. The ethereal layer was washed with water a few times and dried over anhydrous magnesium sulfate. The ether was then distilled off from the ethereal layer and the residue was further distilled in vacuo to obtain 15.7 g of a fraction (b.p. 71°–74° C./0.35–0.38 mmHg) predominantly composed of the propargylic alcohol of formula (II) wherein R¹ is methyl and R² is hydrogen, i.e., [3-(2',4',4'-trimethyl-2'-cyclohexen-1'-yl)-1-butyn-3-ol].

The characteristic peaks in the infrared absorption spectrum (IR) and nuclear magnetic resonance spectrum (NMR) of the above propargylic alcohol are as follows:

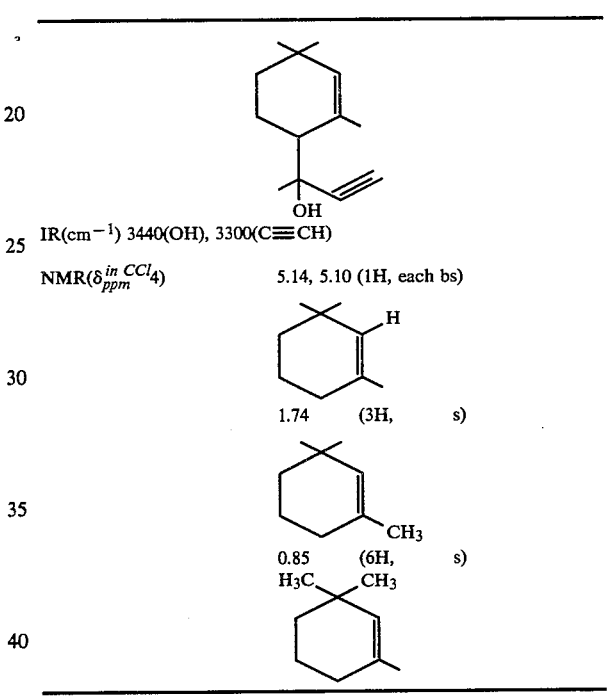

IR(cm⁻¹) 3440(OH), 3300(C≡CH)

NMR($\delta_{ppm}^{in\ CCl_4}$)   5.14, 5.10 (1H, each bs)

1.74   (3H,   s)

0.85   (6H,   s)

(3) Production of ionone (I)

In a three-necked flask of 100 ml capacity, 15 g of the above propargylic alcohol as dissolved in 40 ml of N-methylpyrrolidone was subjected to rearrangement reaction under heating at 180° C.±5° C. in the atmosphere of nitrogen gas for 20 hours. The reaction mixture was poured into a large amount of water and extracted with ether. The ethereal layer was dried over anhydrous magnesium sulfate. The ether was distilled off under reduced pressure and the residue was distilled to obtain 9.6 g of a fraction boiling at 124°–128° C./11–13 mmHg. Gas-chromatographic analysis of this fraction showed that it was a 2:3 mixture of α-ionone and β-ionone.

EXAMPLES 2 TO 6

The procedure of Example 1 was repeated, except that 0.24 mol of one of the acid anhydrides of the formula

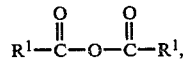

as mentioned in Table 1, was used in lieu of 0.24 mol of acetic anhydride. The resultant mixture of unsaturated ketones (III) and (III') (wherein $R^2$ is hydrogen and $R^1$ is as indicated in Table 1) was ethynylated in the same manner as Example 1. The propargylic alcohol of formula (II) thus obtained (wherein $R^2$ is hydrogen and $R^1$ is as indicated in Table 1) was subjected to rearrangement reaction as in Example 1 in N-methyl pyrrolidone in an amount of 4 times the volume of said alcohol. By this procedure there was obtained the corresponding n-ionone derivative of formula (I) (wherein $R^2$ is hydrogen and $R^1$ is as shown in Table 1). The results are set forth in Table 1:

TABLE 1

| Ex. | Acid anhydride $R^1$ | Unsaturated ketone Yield (III)/(III') (%) ratio | Propargylic alcohol (II) Yield based on (III) (%) | n-Ionone derivative Yield based on (II) (%) |
|---|---|---|---|---|
| 2 | $C_2H_5$ | 88  89/11 | 80 | 70 |
| 3 | n-$C_3H_7$ | 93  95/5 | 83 | 72 |
| 4 | iso-$C_3H_7$ | 90  96/4 | 75 | 61 |
| 5 | n-$C_4H_9$ | 85  93/7 | 78 | 63 |
| 6 | iso-$C_4H_9$ | 84  93/7 | 76 | 58 |

EXAMPLE 7

In an atmosphere of nitrogen gas, 10 g of 3-(2',4',4'-trimethyl-2'-cyclohexen-1'-yl)-1-butyn-3-ol was subjected to thermal rearrangement reaction in the presence of a solvent mentioned in Table 2 in an amount of 3 times the volume of said propargylic alcohol to produce ionone. The results are set forth in Table 2:

TABLE 2

| Solvent | Reaction conditions Temperature (°C.) | Time (hrs.) | Yield of ionone (%) |
|---|---|---|---|
| Dimethylsulfoxide | 160 ± 5 | 30 | 68 |
| Dimethylacetamide | 160 ± 5 | 30 | 65 |

EXAMPLE 8

The procedure of Example 1-(1) and (2) was repeated except that 0.2 mol of methyl-substituted cyclogeraniolene [formula (IV) wherein $R^2=CH_3$] was used in lieu of 0.2 mol of cyclogeraniolene. By this procedure there was obtained a propargylic alcohol of formula (II) (wherein $R^1$ and $R^2=CH_3$), namely, 3-(2',4',4',5'-tetramethyl-2'-cyclohexen-1'-yl)-1-butyn-3-ol, in a yield of 75%; b.p. 80°-86° C./0.3-0.4 mmHg.

In an atmosphere of nitrogen gas, the above propargylic alcohol was heated in 4 volumes of N-methylpyrrolidone at 180°±5° C. for 20 hours. The procedure provided a mixture of α-irone and β-irone in a yield of 63%.

EXAMPLES 9-11

The propargylic alcohol of formula (II) wherein $R^1$ is as indicated in Table 3 and $R^2$ is a hydrogen atom was heated in the absence of a solvent at 160° C. for 20 hours in an atmosphere of nitrogen gas. Conversion of the propargylic alcohols and selectivity to the corresponding ionones, the rearrangement reaction products, are shown in Table 3:

TABLE 3

| Example | $R_1$ | Conversion (%) | Selectivity (%) |
|---|---|---|---|
| 9 | $CH_3$ | 92 | 70 |
| 10 | $C_2H_5$ | 93 | 66 |
| 11 | iso-$C_3H_7$ | 92 | 77 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method for the preparation of ionones and irones which comprises thermally rearranging a propargylic alcohol of the structural formula (II) to obtain a compound of the structural formula (I):

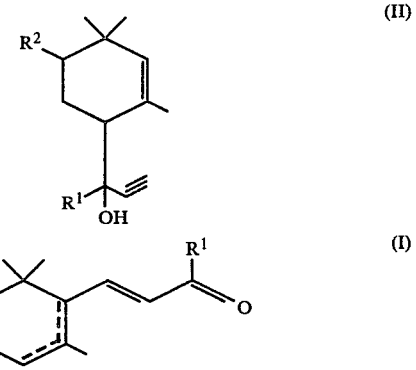

wherein $R^1$ is lower alkyl; $R^2$ is a member selected from the group consisting of hydrogen and methyl; and the dotted line in the structural formula (I) denotes that a double bond exists in either one or the other of the positions indicated.

2. A method as defined by claim 1, wherein said thermal rearrangement is carried out at a temperature within the range of 100° to 400° C.

3. A method as defined by claim 2, wherein said thermal rearrangement is carried out in liquid phase and at a temperature between 130° C. and 300° C.

4. A method as defined by claim 1, wherein a propargylic alcohol of the structural formula:

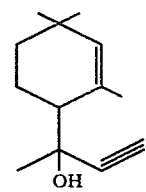

is thermally rearranged to ionone.

5. A method as defined by claim 1, wherein a propargylic alcohol of the formula:

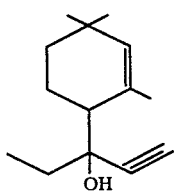

is thermally rearranged to n-methyl ionone.

6. A method as defined by claim 1, wherein a propargylic alcohol of the formula:

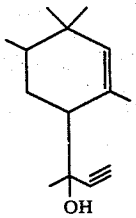

is thermally rearranged to irone.

7. A propargylic alcohol of the structural formula (II):

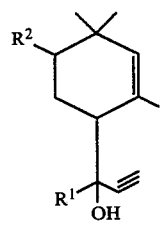

(II)

wherein $R^1$ is lower alkyl; and $R^2$ is a member selected from the group consisting of hydrogen and methyl.

8. A propargylic alcohol of the structural formula (II):

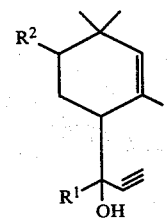

(II)

wherein $R^1$ is methyl; and $R^2$ is a member selected from the group consisting of hydrogen and methyl.

* * * * *